(12) United States Patent  
Ohno et al.

(10) Patent No.: US 8,198,217 B2
(45) Date of Patent: Jun. 12, 2012

(54) COMPOSITION FOR WEEDING

(75) Inventors: Shuji Ohno, Tokyo (JP); Sohei Asakura, Tokyo (JP); Yoshihiro Yamaji, Tokyo (JP); Ryo Hanai, Tokyo (JP); Toshihiro Ikeuchi, Tokyo (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 234 days.

(21) Appl. No.: 12/733,136

(22) PCT Filed: Aug. 6, 2008

(86) PCT No.: PCT/JP2008/064111
§ 371 (c)(1),
(2), (4) Date: Feb. 12, 2010

(87) PCT Pub. No.: WO2009/022598
PCT Pub. Date: Feb. 19, 2009

(65) Prior Publication Data
US 2010/0144526 A1 Jun. 10, 2010

(30) Foreign Application Priority Data
Aug. 10, 2007 (JP) ................. 2007-209507

(51) Int. Cl.
*A01N 43/66* (2006.01)
*A01N 43/54* (2006.01)
*A01P 13/00* (2006.01)

(52) U.S. Cl. ........................ 504/134; 504/136

(58) Field of Classification Search .......... None
See application file for complete search history.

(56) References Cited

U.S. PATENT DOCUMENTS

| 6,458,748 | B1 * | 10/2002 | Yoshimura et al. | 504/243 |
| 7,144,842 | B2 | 12/2006 | Kawasaki et al. | |
| 2003/0004063 | A1 * | 1/2003 | Jimoh | 504/130 |
| 2005/0170964 | A1 * | 8/2005 | Kawasaki et al. | 504/129 |
| 2007/0167328 | A1 * | 7/2007 | Endo et al. | 504/104 |
| 2008/0153704 | A1 * | 6/2008 | Yamaji et al. | 504/136 |

FOREIGN PATENT DOCUMENTS

| JP | 2000-281513 | 10/2000 |
| JP | 2002-145705 | 5/2002 |
| WO | 03/079784 | 10/2003 |
| WO | 2004/010784 | 2/2004 |
| WO | WO 2005092101 A2 * | 10/2005 |

OTHER PUBLICATIONS

International Search Report issued Sep. 2, 2008 in International (PCT) Application No. PCT/JP2008/064111.

* cited by examiner

*Primary Examiner* — Johann Richter
*Assistant Examiner* — Daniel L Branson
(74) *Attorney, Agent, or Firm* — Wenderoth, Lind & Ponack, L.L.P.

(57) ABSTRACT

A mixed composition for weeding useful as a herbicide which is effective against a wide spectrum of weeds, is highly active, has excellent residual activity, and is highly safe for useful plants. It is characterized by containing as an active ingredient a combination of (A) a compound selected among a difluoromethanesulfonylanilide compound represented by the general formula (I):

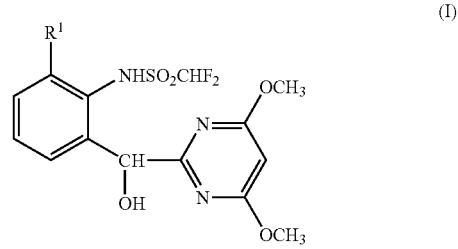

(I)

(wherein $R^1$ is hydrogen, $C_{1-6}$ alkyl, or $C_{2-6}$ alkoxyalkyl) and salts of the compound and (B) at least one member selected among herbicidal aromatic-ring-containing compounds, e.g., indanofan, and herbicidal nitrogenous heterocyclic compounds, e.g., TH-547, nicosulfuron, Flutiacet-methyl, and atrazine.

5 Claims, No Drawings

COMPOSITION FOR WEEDING

TECHNICAL FIELD

The present invention relates to a novel herbicidal composition which is a combination of at least two kinds or more of herbicidally active compounds for selective control of undesirable weeds in culturing useful plants such as agricultural crops as well as to a method for controlling weeds by using the same.

BACKGROUND ART

Herbicides are employed heretofore in the fields of agriculture for improvement of productivity and for labor saving and a great variety of herbicides have been developed depending on types of the cultured plants and weeds to be destroyed. It is considered that preferable herbicides do not cause any phytotoxicity to useful plants and still are effective against as many as possible kinds of weeds, i.e. have a wide weed control spectrum.

It is in recent years, however, that, as a result of continued use of the same kinds of herbicides over so many years, an increasing trend is noted of hardly controllable weeds due to the acquirement of resistance against the herbicides. In addition, the environmental pollution is taken up as a social problem caused by the use of a large amount of herbicides. Accordingly, the desire is directed to a herbicide of high activity having effectiveness against these resistant weeds to exhibit full effectiveness even at a low dosage.

The desires are also directed to a herbicide of long-term sustainable type capable of exhibiting good remaining activity and effectiveness over a long period from before the incipient period to the growth period of the weeds in order to comply with the sporadic generation of weeds caused long during the growth period of useful plants.

With respects to herbicides, furthermore, it is heretofore known that phytotoxicities to the useful plants are caused in the use thereof depending on meteorological conditions such as temperature, wind blow, sun shine and the like, soil conditions such as composition of the soil, pH of the soil and the like, culturing conditions such as depth of transplantation, pooling water depth and the like, and application conditions of the herbicide such as non-uniformity of herbicide application, overly amount of herbicide application and the like so that appearance of herbicides free from phytotoxicity to the useful plants even under variation of these conditions is eagerly desired.

The compound represented by the general formula (I), i.e. component A of the herbicidal composition in the present invention, is known as a compound capable of attaining safety to the useful plants such as rice, wheat, barley, corn, grain sorghum, soybean, cotton, beet, turf, orchard and the like, and exhibiting the excellent herbicidal effectiveness when used singly (JP2000-44546A).

On the other hand, improvements in the herbicidal effectiveness for the compound of general formula (I) have been attempted by combining the compound of general formula (I) with a known compound (JP2000-281513A and WO2004/010784A).

These herbicidal compositions, however, are not always satisfactory to comply with the aforementioned desires so that an important problem in the agricultural field is to develop a herbicidal composition capable of exhibiting still higher effectiveness.

The present invention has been completed with an object to provide a herbicidal composition, as improved for the defects mentioned above in the conventional herbicides, capable of exhibiting high activity against the weeds and a wide weed control spectrum and having a high remaining activity along with high safety to the useful plants.

As a result of earnest investigations made to solve the above-mentioned problems, the inventors have found that a herbicidal composition containing, as the active ingredients, a compound selected from difluoromethane sulfonylanilide compounds represented by the general formula (I)

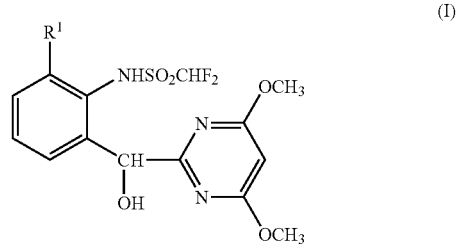

(I)

(in the formula, $R^1$ is a hydrogen atom, alkyl group of 1-6 carbon atoms or alkoxyalkyl group of 2-6 carbon atoms) and salts thereof and a specified compound having herbicidal activity is capable of controlling many kinds of undesirable weeds over a long period of time occurring in the rice cultivation, dry field cultivation, horticulture, turf growing and others and still exhibiting high safety to the useful plants and this effectiveness can be exhibited both before germination and after germination leading to completion of the present invention on the base of this discovery.

Namely, the present invention provides a herbicidal composition which is characterized by containing, as the active ingredient, a combination of (A) a compound selected from the difluoromethane sulfonylanilide compounds represented by the above-given general formula (I) and salts thereof and (B) at least one herbicide compound(s) selected from the following groups (1)-(3) as well as a method for controlling many kinds of undesirable weeds on the paddy field, dry field, horticulture, turf and others over a long period of time by utilizing this herbicidal composition.

(1) nitrogen-containing heterocyclic herbicide compounds:
benzothiazolone-type herbicide compounds such as benazolin, methabenzthiazuron and the like;
bipyridinium-type herbicide compounds such as diquat, paraquat and the like;
imidazolinone-type herbicide compounds such as imazamethabenz, imazamox, imazapic, imazapyr, imazaquin, imazethapyr and the like;
isoxazole-type herbicide compounds such as isoxaflutole and the like;
pyrazole-type herbicide compounds such as pyraflufen-ethyl, pyrasulfotole, topramezone and the like;
pyridazine-type herbicide compounds such as pyridate, maleic hydrazide, norfiurazon, chloridazon and the like;
pyridine-type herbicide compounds such as thiazopyr, picolinafen, clopyralid, fluoroxypyr, picloram, triclopyr, aminopyralid and the like; pyrimidine-type herbicide compounds such as butafenacil, ancymidol, flurprimidol, pyrithiobac-sodium, cloransulam-methyl, diclosulam, florasulam, flumetsulam, metosulam, bromacil, lenacil, terbacil, pyroxsulam, benzfendizone and the like;
triazolinone-type herbicide compounds such as flucarbazone-sodium, propoxycarbazone-sodium, propoxycarbazone, amicarbazone, sulfentrazone, bencarbazone, thiencarbazone and the like;

sulfonylurea-type herbicide compounds such as chlorimuron-ethyl, chlorsulfuron, ethametsulfuron-methyl, flazasulfuron, flupyrsulfuron, foramsulfuron, iodosulfuron, mesosulfuron-methyl, nicosulfuron, oxasulfuron, primisulfuron, prosulfuron, rimsulfuron, sulfometuron-methyl, sulfosulfuron, thifensulfuron-methyl, triasulfuron, tribenuron-methyl, trifloxysulfuron-sodium, triflusulfuron-methyl, tritosulfuron, TH-547(test number) and the like;
thiadiazole-type herbicide compounds such as fluthiacet-methyl and the like;
triazine-type herbicide compounds such as ametryn, atrazine, cyanazine, prometon, prometryn, propazine, simazine, terbumeton, terbuthylazine, terbutryn, trietazine, hexazinone, metamitron, metribuzin and the like; and
triazole-type herbicide compounds such as amitrole, flupoxam and the like.
(2) aromatic ring-containing herbicide compounds:
aromatic amide-type herbicide compounds such as diphenamid, napropamide, pentanochlor, flamprop-M, isoxaben, propyzamide, acetochlor, alachlor, dimethachlor, dimethenamid, metazachlor, metolachlor, pethoxamid, propachlor, propisochlor, S-metolachlor, flufenacet, naptalam and the like;
phenoxycarboxylic acid-type herbicide compounds such as MCPA-thioethyl, clodinafop, diclofop-methyl, fluazifop, fluazifop-P, haloxyfop, haloxyfop-P, haloxyfop-P-methyl, propaquizafop, quizalofop-ethyl, quizalofop-P, quizalofop-P-ethyl, quizalofop-P-tefuryl, 2,4-DB, dichlorprop, dichlorprop-P, mecoprop, mecoprop-P-potassium and the like;
aromatic carboxylic acid-type herbicide compounds such as chlorthal-dimethyl, 2,3,6-TBA, dicamba, quinmerac and the like;
benzofuran-type herbicide compounds such as ethofumesate and the like;
nitrile-type herbicide compounds such as dichlobenil, bromoxynil, ioxynil and the like;
carbamate-type herbicide compounds such as carbetamide, chlorpropham, propham, desmedipham, phenmedipham and the like;
dinitroaniline-type herbicide compounds such as butralin, dinitramine, ethalfluralin, oryzalin, trifluralin and the like;
dinitrophenol-type herbicide compounds such as dinoterb, DNOC and the like;
diphenyl ether-type herbicide compounds such as acifluorfen, fluoroglycofen, fomesafen, lactofen, oxyfluorfen, aclonifen and the like;
N-phenylphthalimide-type herbicide compounds such as cinidon-ethyl, flumiclorac-pentyl, flumioxazin and the like;
aromatic ring-containing urea-type herbicide compounds such as forchlorfenuron, thidiazuron, diflufenzopyr, chlorotoluron, dimefuron, diuron, fluometuron, isouron, karbutilate, linuron, methabenzthiazuron, metoxuron, monolinuron, neburon, tebuthiuron and the like;
benzoylcyclohexadione-type herbicide compounds such as sulcotrione, tembotrione and the like;
phenylpyrazoline-type herbicide compounds such as pinoxaden and the like; and
other aromatic ring-type herbicide compounds such as indanofan and the like.
(3) herbicide compounds having nitrogen-containing aliphatic/alicyclic functional group(s)
cyclohexanedione oxime-type herbicide compounds such as alloxydim, butroxydim, clethodim, cycloxydim, tepraloxydim, tralkoxydim and the like; and
thiocarbamate-type herbicide compounds such as butylate, cycloate, EPTC, pebulate, tri-allate and the like.

Analogues such as salts, acids, esters and amides of the aforementioned herbicide compounds are similarly used as the compound B.

In the compounds represented by the general formula (I) as the component A of the present invention, $R^1$ is a hydrogen atom, straight-chain or branched alkyl group of 1-6 carbon atoms or straight-chain or branched alkoxyalkyl group of 2-6 carbon atoms. As the alkyl group, methyl group, ethyl group, propyl group, isopropyl group, butyl group, isobutyl group, sec-butyl group, tert-butyl group, pentyl group, 1-methylbutyl group and hexyl group are preferred, of which the ethyl group is particularly preferred. As the alkoxyalkyl group, methoxymethyl group, methoxyethyl group, ethoxyethyl group, 3-ethoxypropyl group and 1-methyl-3-methoxybutyl group are preferred, of which the methoxymethyl group is particularly preferred.

The aforementioned compounds used as the component B are known as listed in The Pesticide Manual, 13th edition (published by British Crop Protection Council), SHIBUYA INDEX, 12th edition (published by SHIBUYA INDEX Research Group) and Monthly Fine Chemical, No. 35, Vol. 7 (published in 2006 by CMC Publishing Co.). TH-547 (code number) is 1-(2-chloro-6-propylimidazo[1,2-b]pyridazin-3-ylsulfonyl)-3-(4,6-dimethoxypyrimidin-2-yl)urea which is listed in WO2003/061388A.

The herbicide compounds preferable for the component B are indanofan, TH-547 (code number), nicosulfuron, fluthiacet-methyl and atrazine. Besides, good herbicidal effects are also obtained by the use of two or more compounds of the component B as mixed together.

In the herbicidal composition of the present invention, a combination of the component A and the component B gives a synergistic effect resulting in, as compared with the herbicidal effects obtained with the single use of each active ingredient formulation of which the active ingredient is selected from the components A and B, an earlier exhibition or completion of the herbicidal effect along with a higher herbicidal effect and a wider weed control spectrum as being unpredicted from the herbicidal effects obtained with each single active ingredient formulation.

The herbicidal composition of the present invention enables to control annual weeds in paddy fields including *Echinochloa* species such as early watergrass (*Echinochloa oryzicola*), barnyardgrass (*Echinochloa crus-galli* var. *crus-galli*) and the like; *Cyperus* species such as smallflower umbrella sedge (*Cyperus difformis*), HINA-GAYATSURI (*Cyperus flaccidus*) and the like; weeds of the family of Pontederiaceae such as heartshape false pickerelweed (*Monochoria vaginalis*), MIZU-AOI (*Monochoria korsakowii*) and the like; weeds of the family of Scrophulariaceae such as *Linderina* species, dopatrium (*Dopatrium junceum*) and the like; weeds of the family of Lythraceae such as indian toothcup (*Rotala indica*), HIME-MISO-HAGI (*Ammannia multiflora*) and the like; MIZO-HAKOBE (*Elatine triandra*) and others; perennial weeds including weeds of the family of Alismataceae such as URIKAWA (*Sagittaria pygmaea*), arrow head (*Sagittaria trifolia*) and the like; weeds of the family of Cyperaceae such as tidalmarsh flatsedge (*Cyperus serotinus*), SHIZUI (*Scirpus nipponicus*), KUROGUWAI (*Eleocharis kuroguwai*), rock's bulrush (*Scirpus juncoides*), KOUKIYAGARA (*Scirpus planiculmis*), needle spikerush (*Eleocharis acicularis*) and the like; pondweed (*Potamogeton distinctus*); SERI (*Oenanthe javanica*) and others; weeds in dry fields, lawns, non-agricultural lands and elsewhere such as weeds of the family of Gramineae such as *Echinochloa* species, *Digitaria* species, *Setaria* species, annual bluegrass (*Poa annua*), goosegrass (*Eleusine indica*) and the like;

weeds of the family of Compositae such as annual fleabane (*Erigeron annuus*), philadelphia fleabane (*Erigeron philadelphicus*), Sumatran fleabane (*Conza sumatrensis*) and the like; weeds of the family of *Cyperus* such as purple nutsedge (*Cyperus rotundus*), HIMEKUGU (*Cyperus brevifolius*), KAYATSURI GUSA (*Cyperus microiria*) and the like; weeds of the family of Caryophyllaceae such as MIMINAGUSA (*Cerastium holosteoides*), common chickweed (*Stellaria media*) and the like; weeds of the family of Scrophulariaceae such as Veronica species; weeds of the family of Polygonaceae such as *Polygonum species* and *Rumex* species; weeds of the family of Amaranthaceae such as slender amaranth (*Amaranthus viridis*), livid amaranth (*Amaranthus lividus*) and the like; weeds of the family of Commelinaceae such as common dayflower (*Commelina communis*), tropical spiderwort (*Commelina benghalensis*) and the like; weeds of the family of Equisetaceae such as field horsetail (*Equisetum arvense*), marsh horsetail (*Equisetum palustre*) and the like; weeds of the family of Euphorbiaceae such as *Euphorbia* species; weeds of the family of Umbelliferae such as *Hydrocotyle* species; and others; over a long period of time from before germinating to the growing stage while the composition exhibits high safety to useful plants. Incidentally, the aforementioned "useful plants" include those which have acquired resistance against a certain herbicide or group of herbicides as well as a certain insecticide or group of insecticides by a method of breeding or gene engineering.

The herbicidal composition of the present invention differs depending on the objective case, kinds of the objective useful plants and the undesirable weeds, conditions of the weeds, timing of application, method of application, formulation and others so that the blending proportions and amounts of application can be varied over wide ranges according to need.

As to the compounding proportion, generally speaking, it is desirable to formulate the component A and component B, in a mass ratio ranging from 10:1 to 1:2000 or, preferably, 5:1 to 1:1500 or, particularly preferably, 3:1 to 1:100.

The herbicidal composition of the present invention may be mix-used according to need with insecticides, fungicides, other herbicide compounds, plant growth regulators, microorganisms, fertilizers and the like.

The other herbicide compound which may be mix-used includes, for example, diphenamid, propanil, fenoxaprop-ethyl, metamifop, benfuresate, bentazone, asulam, butachlor, pretilachlor, thenylchlor, sethoxydim, benfluralin, pendimethalin, bifenox, glyphosate, oxadiargyl, oxadiazon, pentoxazone, mefenacet, 2,4-D, clomeprop, MCPA, MCPB, bilanafos, butamifos, bensulide, benzofenap, pyrazoxyfen, dithiopyr, diflufenican, bispyribac-sodium, pyribenzoxim, pyriftalid, pyriminobac-methyl, quinclorac, amidosulfuron, bensulfuron-methyl, cinosulfuron, cyclosulfamuron, ethoxysulfuron, halosulfuron-methyl, imazosulfuron, metsulfuron-methyl, pyrazosulfuron-ethyl, flucetosulfuron, dimepiperate, esprocarb, orbencarb, prosulfocarb, thiobencarb, pyributicarb, dimethametryn, simetryne, carfentrazone-ethyl, flumetsulam, penoxsulam, mesotrione, tefuryltrione, isoproturon, siduron, oxaziclomefone, anilofos, benzobicyclon, prodiamine, cinmethylin, pyraclonil, quinoclamine, triaziflam, etobenzanid, cumyluron, bromobutide, daimuron, cafenstrole and the like. At least one kind of the compound selected from these herbicide compounds may be mix-used.

Furthermore, the herbicidal composition of the present invention may be mix-used with safeners such as cloquintocet-mexyl, fenchlorazole, fenchlorazole-ethyl, mefenpyr, mefenpyr-diethyl, isoxadifen, isoxadifen-ethyl, furilazole, benoxacor, dichlormid, MON 4660, oxabetrinil, cyometrinil, fenclorim, cyprosulfamide, naphthalic anhydride, daimuron, flurazole and the like In the use of the herbicidal composition of the present invention, it can contain, according to need, those additive components under conventional use in pesticidal formulations, though suitable for use as the active ingredients per se.

The additive components are exemplified by carriers such as solid carriers, liquid carriers and the like, surfactants, binders, tackifiers, thickeners, colorants, spreaders, stickers, anti-freezing agents, anticaking agents, disintegrators, stabilizers and the like. In addition thereto, it is optional according to need that a preservative, a plant detritus and the like are used as the additive component. These additive components can be used singly or can be used as a combination of two kinds or more. The following is an explanation as to each additive component.

The solid carrier is exemplified, for example, by: natural minerals such as quartz, clay, kaolinite, pyrophyllite, sericite, talc, bentonite, acid clay, activated clay, attapulgite, zeolite, diatomaceous earth, vermiculite, pearlite, pumice, quartz sand and the like; inorganic salts such as calcium carbonate, ammonium sulfate, sodium sulfate, potassium chloride and the like; organic solid carriers such as fumed silica, synthetic silicic acid, synthetic silicate, starch, cellulose, vegetable powder and the like; plastic carriers such as polyethylene, polypropylene, poly(vinylidene chloride) and the like; and others. These can be used singly or can be used as a combination of two kinds or more.

The liquid carrier is exemplified, for example, by: alcohols including monohydric alcohols such as methanol, ethanol, propanol, isopropanol, butanol and the like and polyhydric alcohols such as ethylene glycol, diethylene glycol, propylene glycol, hexylene glycol, poly(ethylene glycol), poly(propylene glycol), glycerol and the like; polyhydric alcohol compounds such as propylene glycol ethers and the like; ketones such as acetone, methyl ethyl ketone, methyl isobutyl ketone, diisobutyl ketone, cyclohexanone and the like; ethers such as ethyl ether, dioxane, ethyleneglycol monoethyl ether, dipropyl ether, tetrahydrofuran and the like; aliphatic hydrocarbons such as normal paraffins, naphthenes, isoparaffins, kerosenes, mineral oils and the like; aromatic hydrocarbons such as benzene, toluene, xylene, solvent naphtha, alkyl benzenes, alkyl naphthalenes and the like; halogenated hydrocarbons such as dichloroethane, chloroform, carbon tetrachloride and the like; esters such as ethyl acetate, diisopropyl phthalate, dibutyl phthalate, dioctyl phthalate, dimethyl adipate and the like; lactones such as γ-butyrolactone and the like; amides such as dimethylformamide, diethylformamide, dimethylacetamide, N-alkylpyrrolidinone and the like; nitriles such as acetonitrile and the like; sulfur compounds such as dimethyl sulfoxide and the like; vegetable oils such as soybean oil, rapeseed oil, cottonseed oil, castor oil and the like; water; and others. These can be used singly or can be used as a combination of two kinds or more.

The surfactant is exemplified, for example, by: nonionic surfactants such as sorbitan fatty acid esters, polyoxyethylene sorbitan fatty acid esters, sucrose fatty acid esters, polyoxyethylene fatty acid esters, polyoxyethylene resinate esters, polyoxyethylene fatty acid diesters, polyoxyethylene alkyl ethers, polyoxyethylene alkylphenyl ethers, polyoxyethylene dialkyl phenyl ethers, polyoxyethylene alkyl phenyl ether-formalin condensates, polyoxyethylene-polyoxypropylene block polymers, alkyl polyoxyethylene-polypropylene block polymer ethers, polyoxyethylenealkylamines, polyoxyethylene fatty acid amides, polyoxyethylene fatty acid bisphenyl ethers, polyalkylene benzyl phenyl ethers, polyoxyalkylene styrylphenyl ethers, acetylene diols, polyoxyalkylene-added acetylene diols, polyoxyethylene ether-type silicones, ester-type silicones, fluorine surfactants, polyoxyethylene castor oils, hydrogenated polyoxyethylene castor oils and the like; anionic surfactants such as alkyl sulfate salts, polyoxyethylene alkyl ether sulfate salts, polyoxyethylene alkyl phenyl ether sulfate salts, polyoxyethylene styryl phenyl ether sulfate salts, alkylbenzenesulfonate salts, lignin sulfonate salts, alkylsulfosuccinate salts, naphthalenesulfonate salts, alkylnaphthalene sulfonate salts, salts of formalin condensate of naphthalene sulfonic acid, salts of formalin condensate of alkylnaphthalene sulfonic acid, fatty acid salts, polycarboxylate salts, N-methyl-fatty acid sarcosinate, resinates, polyoxyethylene alkyl ether phosphate salts, polyoxyethylene alkyl phenyl ether phosphate salts and the like; cationic surfactants such as laurylamine hydrochloride salts, stearylamine hydrochloride salts, oleylamine hydrochloride salts, stearylamine acetate salts, stearylaminopropylamine acetate salts, alkylamine salts including alkyltrimethylammonium chloride, alkyldimethylbenzalkonium chloride and the like; ampholytic surfactants such as amino acid or betaine surfactants and the like; and so on. These surfactants can be used singly or can be used as a combination of two kinds or more.

The binder and tackifier are exemplified, for example, by carboxymethylcellulose and salts thereof, dextrin, water-soluble starch, xanthan gum, guar gum, sucrose, poly(vinylpyrrolidone), gum arabic, poly(vinyl alcohol), poly(vinyl acetate), sodium polyacrylate, poly(ethylene glycol) with an average molecular weight of 6000 to 20000, polyethylene oxide with an average molecular weight of 100000 to 5000000, phospholipid (for example, cephalin, lecitin and the like) and so on.

The thickener is exemplified, for example, by: water-soluble polymers such as xanthan gum, guar gum, carboxymethylcellulose, poly(vinylpyrrolidone), carboxyvinyl polymers, acrylic polymers, starch derivatives and water-soluble polysaccharides; inorganic fine powders such as high-purity bentonite and fumed silica (white carbon); and so on.

The colorant is exemplified, for example, by inorganic pigments such as iron oxide, titanium oxide and Prussian blue, organic dyes such as alizarin dye, azo dye and metal phthalocyanine dye, and so on.

The spreader is exemplified, for example, by silicon-type surfactants, cellulose powder, dextrin, modified starch, polyaminocarboxylic acid chelate compounds, crosslinked poly(vinylpyrrolidone), copolymers of maleic acid with a styrene compound, (meth)acrylic acid copolymers, half esters of a polymer consisting of polyhydric alcohol with dicarboxylic anhydride, water-soluble salts of polystyrene-sulfonic acid and the like.

The sticker is exemplified, for example, by paraffin, terpene, polyamide resins, polyacrylate, polyoxyethylene, wax, polyvinyl alkyl ether, alkylphenol-formalin condensates, phosphate esters of starch, synthetic resin emulsions and the like.

The antifreezing agent is exemplified, for example, by polyhydric alcohols such as ethylene glycol, diethylene glycol, propylene glycol, glycerol and the like, and so on.

The anticaking agent is exemplified, for example, by polysaccharides such as starch, alginic acid, mannose, galactose and the like, poly(vinylpyrrolidone), fumed silica (white carbon), ester gum, petroleum resins and the like.

The disintegrator is exemplified, for example, by sodium tripolyphosphate, sodium hexametaphosphate, metal stearates, cellulose powder, dextrin, methacrylate-type copolymers, poly(vinylpyrrolidone), polyaminocarboxylic acid chelate compounds, sulfonated styrene/isobutylene/maleic anhydride copolymers, starch/polyacrylonitrile graft copolymers and the like.

The stabilizer is exemplified, for example, by: desiccants such as zeolite, calcined lime, magnesium oxide and the like; ultraviolet absorbers such as salicylic acid compounds, benzophenone compounds and the like; antioxidants such as phenol compounds, amine compounds, sulfur compounds, phosphoric acid compounds and the like; and so on.

The preservative is exemplified, for example, by sodium benzoate, sodium p-hydroxybenzoate, potassium sorbate, 1,2-benzthiazolin-3-one and the like.

The plant detritus is exemplified, for example, by sawdust, coconut shell, corn cob, tobacco stalk and the like.

When the aforementioned additive component is contained in the herbicidal composition of the present invention, a content thereof is selected in the range of, on a mass basis, usually 5 to 95% or, preferably, 20 to 90% for a carrier, usually 0.1 to 30% or, preferably, 0.5 to 10% for a surfactant, and 0.1 to 30% or, preferably, 0.5 to 10% as other additives.

The herbicidal composition of the present invention can be employed as prepared in any desired formulations including liquid formulations, emulsifiable concentrates, wettable powders, dust formulations, oil solutions, water dispersible granules, flowable agents, emulsion waters, granules, fine granules, jumbo formulations, suspo-emulsions, microcapsules and others.

In conducting preparation of the formulation, it is optional to prepare a mixed composition of pesticides other than the component A and component B such as, for example, other herbicide compounds, insecticides, fungicides, plant growth regulators, safeners as well as fertilizers and the like.

In the use of the herbicidal composition of the present invention, it is optional to use it by direct application or to be diluted to a concentration in accordance with the object of use for application onto stalks and leaves, application to soil, application to water surface and so on. It is also optional that the herbicidal composition of the present invention is used as mixed together in advance or used as consecutively mixed according to the object.

The amounts of the active ingredients in the formulation of the herbicidal composition of the present invention are selected appropriately according to need. When it is in the form of a dust formulation, fine granules or granules, it is preferable that the selection is made in the range of 0.01 to 80% (by weight) or, preferably, 0.05 to 50% (by weight). When it is in the form of an emulsifiable concentrate, liquid formulation, flowable agent, wettable powders or water dispersible granules, it is preferable that the selection is made in the range of 1 to 90% (by weight) or, preferably, 5 to 80% (by weight).

In the present invention, the amount of the herbicidal composition for application is varied depending on the kinds of active ingredients therein, objective weeds, trend of occurrence, environmental conditions, formulation form for use and others.

In the case of a dust formulation, fine granules or granules, selection for use is made in the range of 0.1 g to 5 kg or, preferably, 0.5 g to 1 kg of the active ingredients per 10 ares.

In the case of an emulsifiable concentrate, liquid formulation, flowable agent, wettable powders, water dispersible granules or the like which is diluted with water for use, selection for use is made for concentration of the active ingredients usually in the range of 10 to 100,000 ppm.

BEST MODE FOR PRACTICING THE INVENTION

In the next place, the best mode for practicing the present invention is described by way of Examples. The types and compounding proportions of the active ingredients and additives can be changed in wide ranges without being limited thereto.

In the Examples below, the compound A-1 is the compound of the general formula (I) in which the $R^1$ is a methoxymethyl group, that is pyrimisulfan or, namely, 2-[(4,6-dimethoxypyrimidin-2-yl)hydroxymethyl]-6-methoxymethyl-N-difluoromethanesulfonylanilide. In the following description, incidentally, "part" means "part by weight".

EXAMPLE 1

Wettable Powder

The following materials were mixed together and pulverized so as to give a wettable powder.

| | |
|---|---|
| Compound A-1 | 5 parts |
| indanofan | 15 parts |
| polyoxyethylene styrylphenyl ether | 2 parts |
| sodium salt of β-naphthalene sulfonic acid-formalin condensate | 2 parts |
| diatomaceous earth | 20 parts |
| clay | 56 parts |

EXAMPLE 2

Wettable Powder

The following materials were mixed together and pulverized so as to give a wettable powder.

| | |
|---|---|
| Compound A-1 | 5 parts |
| TH-547 | 10 parts |
| polyoxyethylene styrylphenyl ether | 2 parts |
| sodium salt of β-naphthalene sulfonic acid-formalin condensate | 2 parts |
| diatomaceous earth | 20 parts |
| clay | 56 parts |

EXAMPLE 3

Water Dispersible Granules

The following materials were mixed together and pulverized followed by addition of an appropriate water thereto for kneading, so as to perform an extrusion granulation of the mixture through a screen of 0.7 mm mesh opening diameter

| | |
|---|---|
| Compound A-1 | 10 parts |
| nicosulfuron | 10 parts |
| sodium lignin sulfonate | 5 parts |
| sodium salt of naphthalene sulfonic acid-formalin condensate | 5 parts |
| poly(vinyl alcohol) | 1 part |
| diatomaceous earth | 30 parts |
| clay | 39 parts |

The thus obtained granulation materials were dried to give water dispersible granules.

EXAMPLE 4

Water Dispersible Granules

The following materials were mixed together and pulverized followed by addition of an appropriate water thereto for kneading, so as to perform an extrusion granulation of the mixture through a screen of 0.7 mm mesh opening diameter.

| | |
|---|---|
| Compound A-1 | 15 parts |
| fluthiacet-methyl | 5 parts |
| sodium lignin sulfonate | 5 parts |
| sodium salt of naphthalene sulfonic acid-formalin condensate | 5 parts |
| poly(vinyl alcohol) | 1 part |
| fumed silica | 2 parts |
| diatomaceous earth | 30 parts |
| clay | 37 parts |

The thus obtained granulation materials were dried to give water dispersible granules.

EXAMPLE 5

Water Dispersible Granules

The following materials were mixed together and pulverized followed by addition of an appropriate water thereto for kneading, so as to perform an extrusion granulation of the mixture through a screen of 0.7 mm mesh opening diameter.

| | |
|---|---|
| Compound A-1 | 5 parts |
| atrazine | 30 parts |
| sodium lignin sulfonate | 5 parts |
| sodium salt of naphthalene sulfonic acid-formalin condensate | 5 parts |
| poly(vinyl alcohol) | 1 part |
| fumed silica | 2 parts |
| diatomaceous earth | 20 parts |
| clay | 32 parts |

The thus obtained granulation materials were dried to give water dispersible granules.

EXAMPLE 6

Flowable Agent

The following materials were mixed together with a high-speed agitator and pulverized with a wet-process grinder (beads mill) to give a flowable agent.

| | |
|---|---|
| Compound A-1 | 2 parts |
| indanofan | 4 parts |
| polyoxyethylene styrylphenyl ether | 3 parts |
| ammonium sulfate | |
| sodium salt of alkylsulfosuccinate | 1 part |
| xanthan gum | 0.2 part |
| bentonite | 0.5 part |
| propylene glycol | 10 parts |
| water | 79.3 parts |

EXAMPLE 7

Flowable Agent

The following materials were mixed together with a high-speed agitator and pulverized with a wet-process grinder (beads mill) to give a flowable agent.

| | |
|---|---|
| Compound A-1 | 3 parts |
| atrazine | 20 parts |
| polyoxyethylene styrylphenyl ether ammonium sulfate | 3 parts |
| sodium salt of alkylsulfosuccinate | 1 part |
| xanthan gum | 0.1 part |
| bentonite | 0.5 part |
| propylene glycol | 10 parts |
| water | 62.4 parts |

EXAMPLE 8

Granules

The following materials were mixed together with an appropriate water for kneading followed by an extrusion granulation through a screen of 1.0 mm mesh opening diameter.

| | |
|---|---|
| Compound A-1 | 1 part |
| TH-547 | 2 parts |
| sodium alkylbenzenesulfonate | 1 part |
| pregelatinized starch | 3 parts |
| bentonite | 10 parts |
| calcium carbonate | 83 parts |

The thus obtained granulation materials were dried to give granules.

In the following, a description is given by way of Test Examples to show effectiveness caused by the herbicidal compositions of the present invention.

TEST EXAMPLE 1

Weed Control Effect Test on Paddy Fields

A plastic pot of 1/20000 are area was each filled with a paddy field soil which was manured and shuffled followed by sowing of the respective seeds of early watergrass (ECHOR), heartshape false pickerelweed (MOOVA), rock's bulrush (SCIJO) and marsh dayflower (ANEKE) and burying of tuberous roots of tidalmarsh flatsedge (CYPSE) followed by pooling of water in a water depth of 1 cm. And, paddy rice plants (Or) at the two-leaves stage were transplanted to the same pot and grown in a greenhouse. Thereafter, on the day when the early watergrass had reached its 2.5 leaves stage, pooling of water was undertaken in order to make the water depth to 3 cm and agents each prepared by dilution of a specified amount of the wettable powder prepared in the same manner as in Example 1 and 2 with water was applied onto the water surface, respectively. Then, growing was continued keeping the pooling water depth of 3 cm to record the weed control effect and the extent of phytotoxicity on the 25th day from the treatment as indexes according to the criteria given in Table 1. The results are shown in Table 2. The dosages are given in terms of the amount of the active ingredients per 10 ares area.

TABLE 1

| Index | Weed control effect and extent of phytotoxicity (Growth inhibition degree in portions above soil level) |
|---|---|
| 10 | 95% or higher growth inhibition |
| 9 | not less than 85% but less than 95% growth inhibition |
| 8 | not less than 75% but less than 85% growth inhibition |
| 7 | not less than 65% but less than 75% growth inhibition |
| 6 | not less than 55% but less than 65% growth inhibition |
| 5 | not less than 45% but less than 55% growth inhibition |
| 4 | not less than 35% but less than 45% growth inhibition |
| 3 | not less than 25% but less than 35% growth inhibition |
| 2 | not less than 15% but less than 25% growth inhibition |
| 1 | not less than 5% but less than 15% growth inhibition |
| 0 | less than 5% growth inhibition |

TABLE 2

| Compound | Dosage, g a.i./10a | OR | ECHOR | MOOVA | SCIJO | CYPSE | ANEKE |
|---|---|---|---|---|---|---|---|
| Compound A-1 | 3 | 0 | 7 | 7 | 8 | 8 | 2 |
| indanofan | 15 | 0 | 6 | 5 | 3 | 1 | 5 |
| Compound A-1 + indanofan | 3 + 15 | 0 | 10 | 10 | 10 | 10 | 10 |
| Compound A-1 | 3 | 0 | 7 | 7 | 8 | 8 | 2 |
| TH-547 | 7 | 0 | 7 | 7 | 6 | 6 | 4 |
| Compound A-1 + TH-547 | 3 + 7 | 0 | 10 | 10 | 10 | 10 | 8 |

TEST EXAMPLE 2

Weed Control Effect Test by Stems-and-Leaves Treatment

A plastic pot of 1/2000 are area was each filled with a dry-field soil where the respective seeds of corn (ZEAMX), pitted morningglory (IPOLA), velvet leaf (ABUTH) and lamb's-quarters (CHEAL) were sowed and tuberous roots of yellow nutsedge (CYPES) were buried followed by pooling of water from the bottom part of the pot. These seeds and tuberous roots were grown in a greenhouse. On the day when the pitted morningglory had reached its 4 leaves stage, a stems-and-leaves treatment was undertaken on the whole plant bodies with agents each prepared by dilution of a specified amount of the water-dispersible granules prepared in the same manner as in Example 3, 4 and 5 with water, respectively. Thereafter, growing was continued in the glasshouse to record the weed control effect and the extent of phytotoxicity on the 30th day from the treatment as indexes according to the criteria given in Table 1. The results are shown in Table 3. The dosages are given in terms of the amount of the active ingredients per hectare (ha).

TABLE 3

| Compound | Dosage, g a.i./ha | ZEAMX | IPOLA | ABUTH | CHEAL | CYPES |
|---|---|---|---|---|---|---|
| Compound A-1 | 10 | 0 | 6 | 5 | 1 | 7 |
| nicosulfuron | 35 | 0 | 3 | 2 | 8 | 4 |
| Compound A-1 + nicosulfuron | 10 + 35 | 0 | 10 | 10 | 10 | 10 |
| Compound A-1 | 10 | 0 | 6 | 5 | 1 | 7 |
| fluthiacet-methyl | 5 | 0 | 3 | 9 | 8 | 2 |
| Compound A-1 + fluthiacet-methyl | 10 + 5 | 0 | 10 | 10 | 10 | 10 |
| Compound A-1 | 10 | 0 | 6 | 5 | 1 | 7 |
| atrazine | 1000 | 0 | 3 | 3 | 8 | 3 |
| Compound A-1 + atrazine | 10 + 1000 | 0 | 10 | 10 | 10 | 10 |

INDUSTRIAL UTILIZABILITY

The herbicidal composition of the present invention has a wide weed control spectrum against undesirable weeds occurring in the growing area of useful plants and further, as compared with existing herbicides, has a longer period suitable for the chemical treatment so that generation of undesirable weeds can be reduced over a long period of time still exhibiting safety against phytotoxicity to the useful plants so as to enable to contribute toward labor saving in culturing and increase in production.

The invention claimed is:

1. A herbicidal composition which comprises, as the active ingredient, a combination of:
    (A) at least one compound selected from difluoromethane sulfonylanilide compounds represented by the general formula (I)

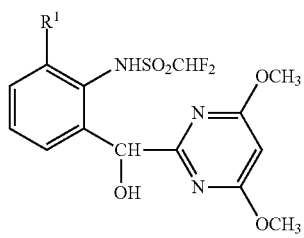

(in the formula, R1 is a hydrogen atom, alkyl group of 1 to 6 carbon atoms or alkoxyalkyl group of 2 to 6 carbon atoms) and salts thereof; and
    (B) at least one nitrogen-containing heterocyclic herbicide compound selected from TH-547, nicosulfuron, fluthiacet-methyl and atrazine.

2. The herbicidal composition according to claim 1 wherein the compound A and the compound B are contained in a mass ratio in the range of 10:1 to 1:2000.

3. A method for controlling growth of undesirable weeds in the area of useful plants, which comprises applying the herbicidal composition according to claim 1 in a herbicidally effective amount to the area where the useful plants are to be grown or under growing.

4. The method according to claim 3 wherein the useful plant is a paddy field crop, dry field crop, horticultural crop or plant cultured on turf, orchard or non-agricultural land.

5. The method according to claim 3 wherein the area where the useful plants are to be grown or under growing is a paddy field, dry field, turf or non-agricultural land.

* * * * *